United States Patent [19]

Lovegrove

[11] Patent Number: 4,465,583
[45] Date of Patent: Aug. 14, 1984

[54] ELECTROPHORETIC SEPARATOR

[75] Inventor: Peter C. Lovegrove, Didcot, England

[73] Assignee: United Kingdom Atomic Energy Authority, London, England

[21] Appl. No.: 506,027

[22] Filed: Jun. 20, 1983

[30] Foreign Application Priority Data

Jul. 7, 1982 [GB] United Kingdom ............... 8219682
Apr. 7, 1983 [GB] United Kingdom ............... 8309458

[51] Int. Cl.³ .................... G01N 27/26; G01N 27/28
[52] U.S. Cl. ........................... 204/299 R; 137/625.11;
137/625.44; 137/625.21
[58] Field of Search ............ 204/299 R; 137/625.11,
137/625.44, 625.21

[56] References Cited

U.S. PATENT DOCUMENTS

| 406,141 | 7/1889 | Johnson | 137/625.11 |
|---|---|---|---|
| 2,600,099 | 6/1952 | Detrez | 137/625.21 |
| 3,040,776 | 7/1962 | Russell | 137/625.44 |
| 3,096,788 | 7/1963 | Talbot et al. | 137/625.11 |
| 3,297,052 | 1/1967 | Robinson | 137/625.21 |
| 3,458,427 | 7/1969 | Strickler | 204/299 R |
| 3,616,453 | 10/1971 | Philpot | 204/299 R |
| 3,616,455 | 10/1971 | Munchhausen | 204/299 R |
| 3,844,926 | 10/1974 | Smyth et al. | 204/299 R |

FOREIGN PATENT DOCUMENTS 1433620  4/1976  United Kingdom .

Primary Examiner—John F. Niebling
Assistant Examiner—B. J. Boggs, Jr.
Attorney, Agent, or Firm—William R. Hinds

[57] ABSTRACT

A continuous flow electrophoretic separator 10 includes a multiple valve assembly 60 to enable each of a plurality of outlet streams of liquid to be diverted to one of two or more outlets 54 or 56 independently of the other streams, and also to enable the rate of flow of each outlet stream to be controlled independently of the other streams.

16 Claims, 10 Drawing Figures

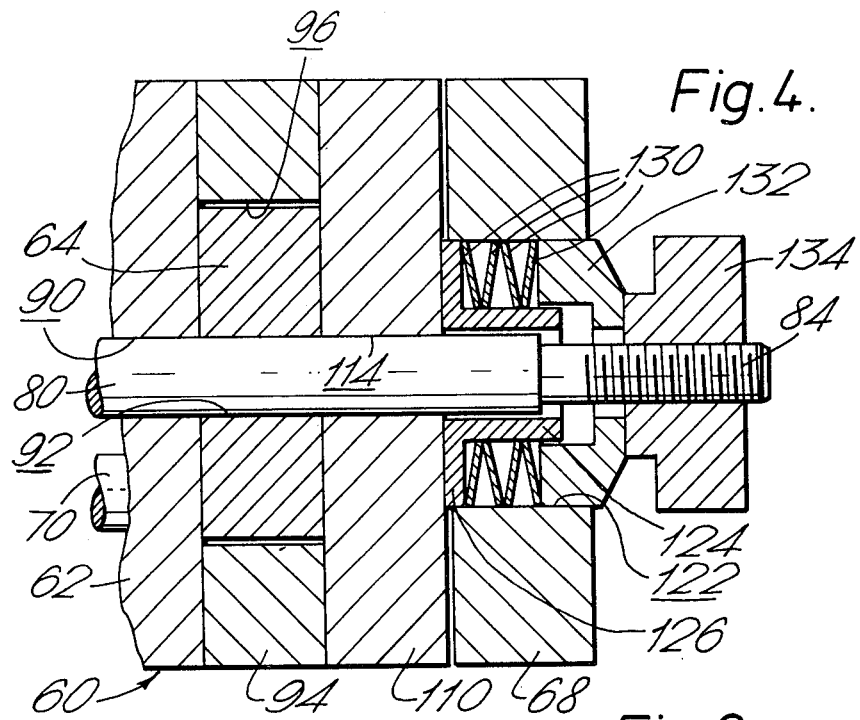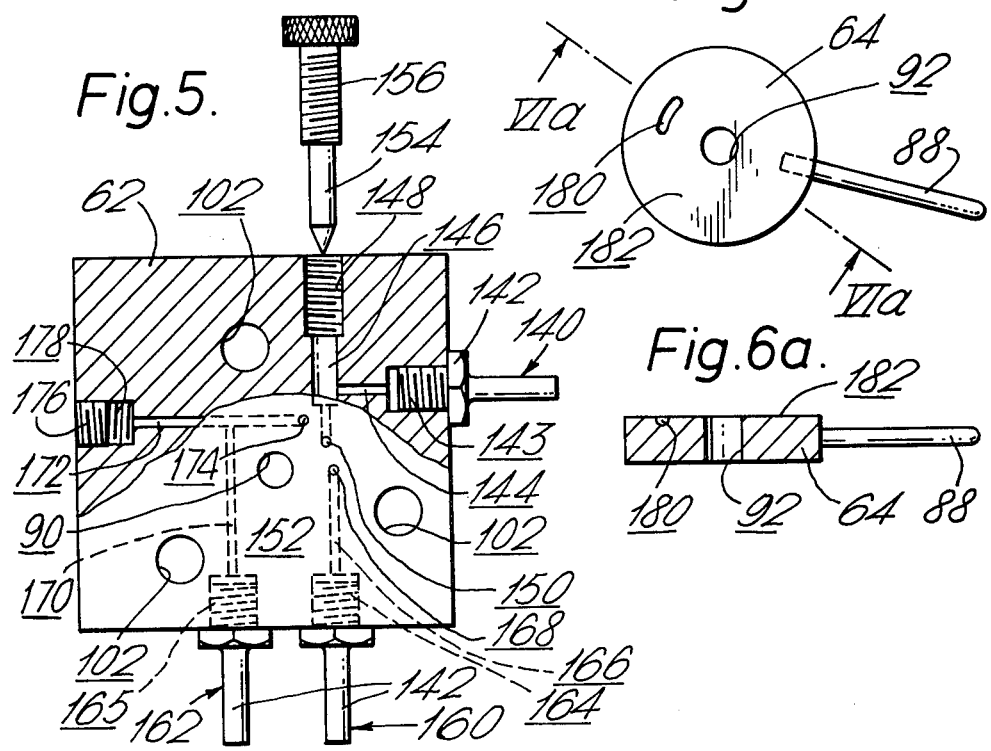

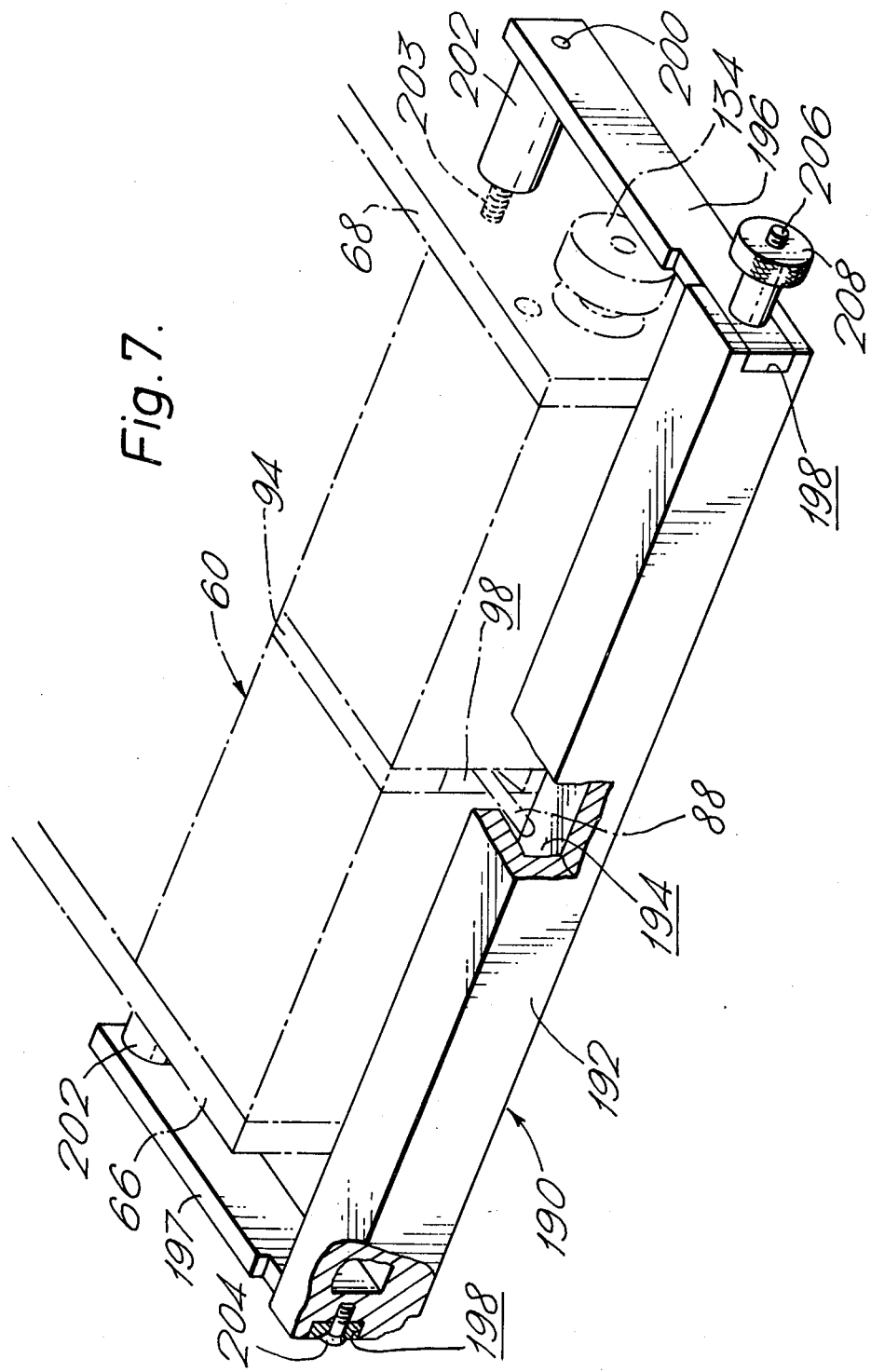

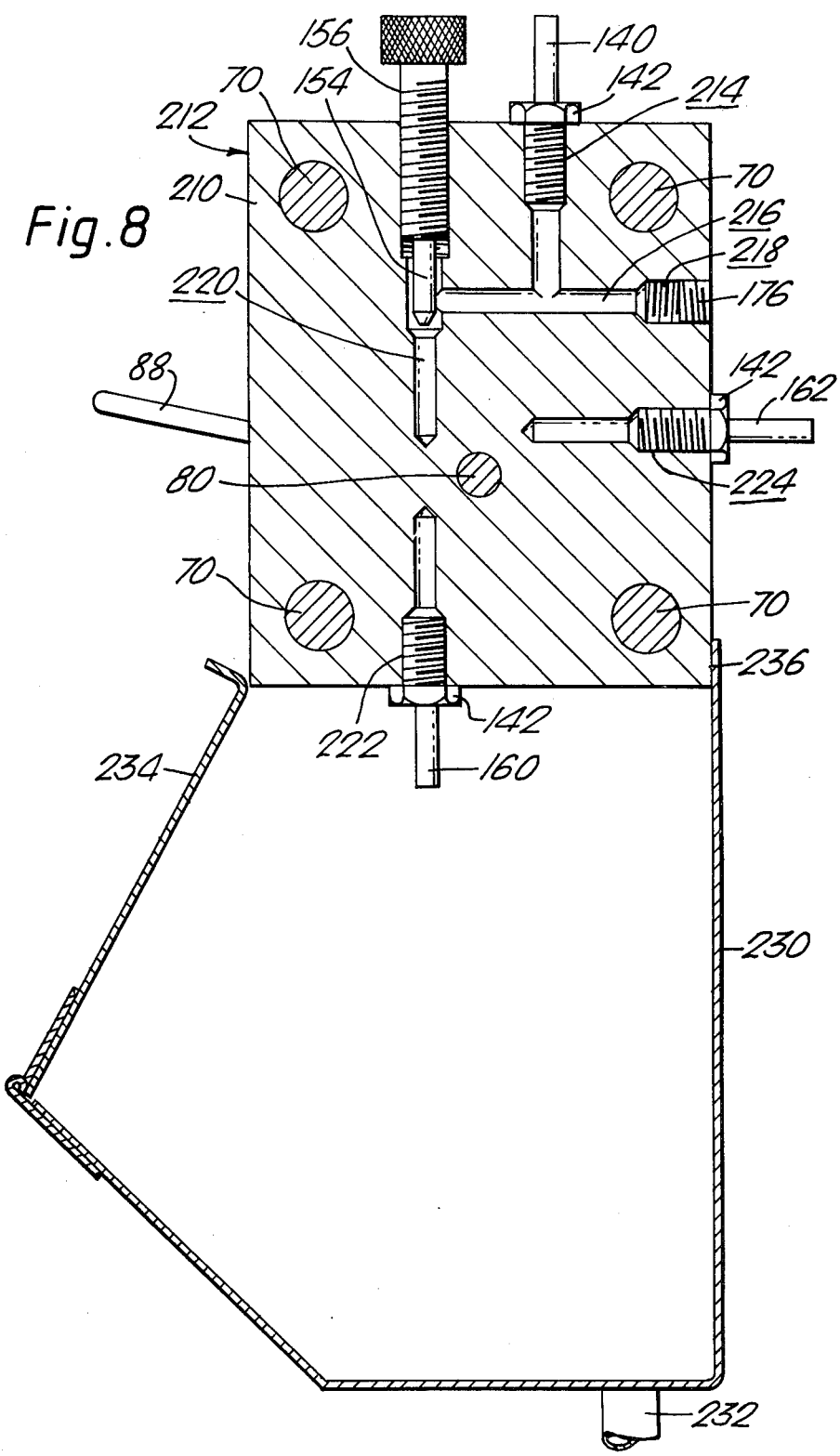

ELECTROPHORETIC SEPARATOR

This invention relates to a continuous flow electrophoretic separator, having a plurality of outlets therefrom.

A continuous flow electrophoretic separator comprises a cylindrical stator, a concentric tubular rotor defining an annular chamber between the stator and the rotor, an electrode incorporated in the stator, an electrode incorporated into the rotor, means for causing a carrier liquid to flow through the chamber, and means for injecting a migrant material into the carrier liquid. In operation, an electric field is applied radially across the annular chamber between the electrodes, carrier liquid is caused to flow through the annular chamber, and the rotor is rotated about the stator so as to stabilise laminar flow in the chamber. Migrant material injected into the carrier liquid is thus subjected to electrophoretic separation.

An example of a continuous flow electrophoretic separator is described in UK Patent Specification No. 1,186,184 (U.S. Pat. No. 3,616,453), and modification to that example is described in UK Patent Specifications Nos. 1,431,888 and 1,431,887 (U.S. Pat. No. 3,844,926), the aforementioned specifications being incorporated by reference herein. Such separators may be used to fractionate an inlet stream into a plurality of outlet streams.

The invention provides a continuous flow electrophoretic separator comprising a rotor, a stator, an annular chamber defined between the rotor and the stator, and a plurality of discharge ducts communicating with the chamber, wherein there is provided a multiple valve assembly comprising a plurality of valve units, each valve unit being connectable to a respective one of the discharge ducts and comprising means for controlling independently of the other valve units the rate of flow of a liquid therethrough, and means for diverting the liquid flowing through said valve unit to one of a plurality of outlet ports. Each diverting means may be operable independently of the other diverting means.

Preferably, the diverting means comprises a valve body with an inlet port connectable to one of the discharge ducts, a plurality of outlet ports, an inlet valve port, a plurality of outlet valve ports, a duct within the valve block communicating between the inlet port and the inlet valve port, and ducts within the valve body each communicating between one of the outlet ports and a corresponding one of the outlet valve ports, and a diverter member defining a diversion duct and turnable about an axis between positions in which the diversion duct provides communication between the inlet valve port and any one of the outlet valve ports.

Preferably, the inlet valve port and the outlet valve ports extend from a plane face of the valve body, and the diversion duct may comprise a groove on a face of the diverter member adjacent to the plane face of the valve body.

Preferably, each valve body has two outlet ports, and the inlet valve port, the first outlet valve port and the second outlet valve port lie on an arc of a circle centred on the axis, the inlet valve port desirably being midway between the first outlet valve port and the second outlet valve port.

Preferably, resilient means are provided to urge the valve bodies and the diverter members together. The invention will now be further described by way of example only and with reference to the accompanying drawings, in which:

FIG. 4 is an axial sectional view of part of the multiple valve assembly of FIG. 3 as assembled, viewed along the line IV–IV of FIG. 3

FIG. 5 is a partly broken away view in the direction of arrow V of FIG. 3;

FIG. 6 is a view in the direction of arrow VI of FIG. 3;

FIG. 6a is a sectional view along the line VIa–VIa of FIG. 6;

FIG. 7 is a perspective view partly broken away of a modification to the multiple valve assembly of FIG. 2; and FIG. 8 is a sectional view through an alternative multiple valve assembly.

Figure 1:
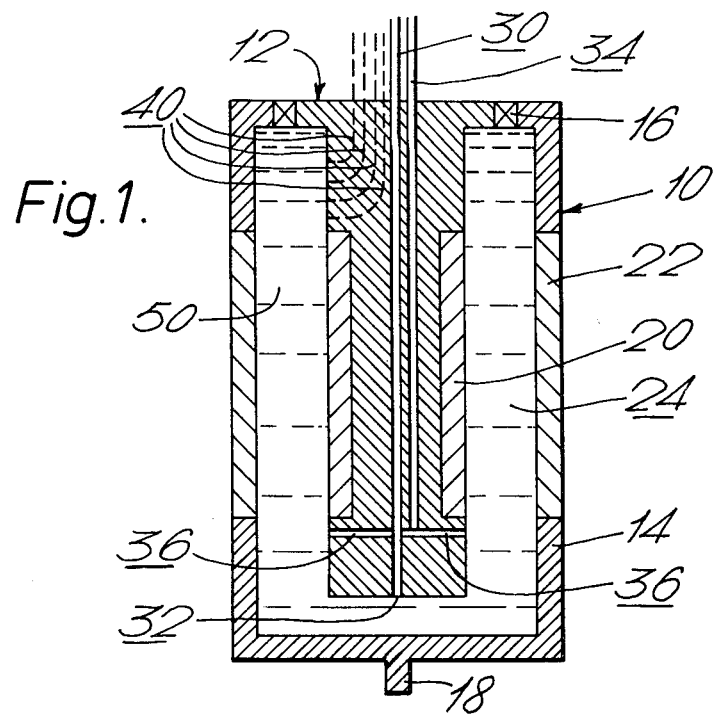
FIG. 1 is a diagrammatic medial sectional representation of an electrophoretic separator.

Referring to FIG. 1, an electrophoretic separator 10 is shown similar in principle to those described in the aforementioned patent specifications. The separator 10 comprises a rigidly mounted cylindrical stator 12, and a concentric tubular rotor 14 rotatably connected to the stator 12 by a bearing 16 at its upper end and drivable by means of a stub shaft 18 attached to the lower end of the rotor 14. The stator 12 incorporates a cylindrical electrode 20 along a portion of its length, and the rotor 14 incorporates a tubular electrode 22 in opposed relationship to the electrode 20 so as to define an annular chamber 24 between the two electrodes 20 and 22 in which, in operation of the separator 10, electrophoresis takes place. A duct 30 extends through the stator 12 to a port 32 at the lower end of the stator 12, and a duct 34 extends through the stator 12 to communicate with radial slots 36 (only two are shown) around the perimeter of the stator 12 below the lower end of the electrode 20. Thirty discharge ducts 40 (only four of which are indicated by broken lines) extend through the stator 12 from thirty axially displaced positions on the surface of the stator 12 above the upper end of the electrode 20. For further details with respect to the construction of the electrophoretic separator 10 reference is directed to the aforementioned specifications.

In operation of the separator 10, a potential difference is applied between the two electrodes 20 and 22 so as to set up a radial electric field across the annular chamber 24, and the rotor 14 is rotated about the stator 12. A carrier liquid 50 is supplied down the duct 30 to the port 32, flowing upwards between the stator 12 and rotor 14 to emerge through the discharge ducts 40. A migrant material is caused to flow down the duct 34 to emerge from the slots 36 into the carrier liquid 50, and is carried upwards through the annular chamber 24. As a result of its passage through the electric field, the migrant is electrophoretically separated into its components, which follow radially separate paths through the chamber 24, and hence emerge through different discharge ducts 40. The flow of carrier liquid 50 and migrant material through the separator 10 is thus fractionated into thirty outlet streams emerging from the thirty ducts 40.

Figure 2:
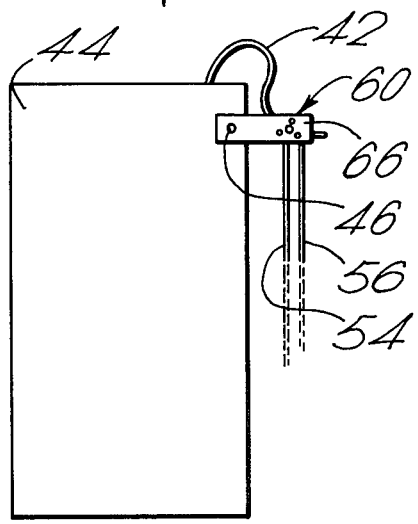
FIG. 2 is a side view of the electrophoretic separator of FIG. 1, including a multiple valve assembly.
Figure 2A:
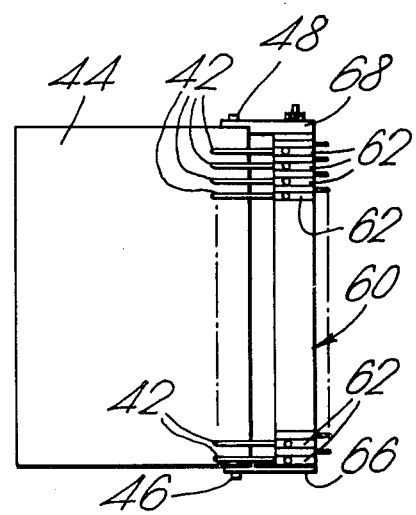
FIG. 2a is a view along the direction of arrow A of FIG. 2.

As shown in FIG. 2 and 2a, thirty tubes 42 (only six of which are shown) extend from the upper ends of the ducts 40 of FIG. 1 to a multiple valve assembly 60 attached by bolts 46 and 48 to a casing 44 enclosing the separator 10 of FIG. 1. Each tube 42 is connected to one of the ducts 40E.

The multiple valve assembly 60 comprises thirty valve blocks 62 (only six of which are shown), to each of which one of tubes 42 is connected and from each of which two outlet tubes 54 and 56 extend, the blocks 62 being clamped between a stainless steel left hand end plate 66 and a stainless steel right hand end plate 68.

Figure 3:
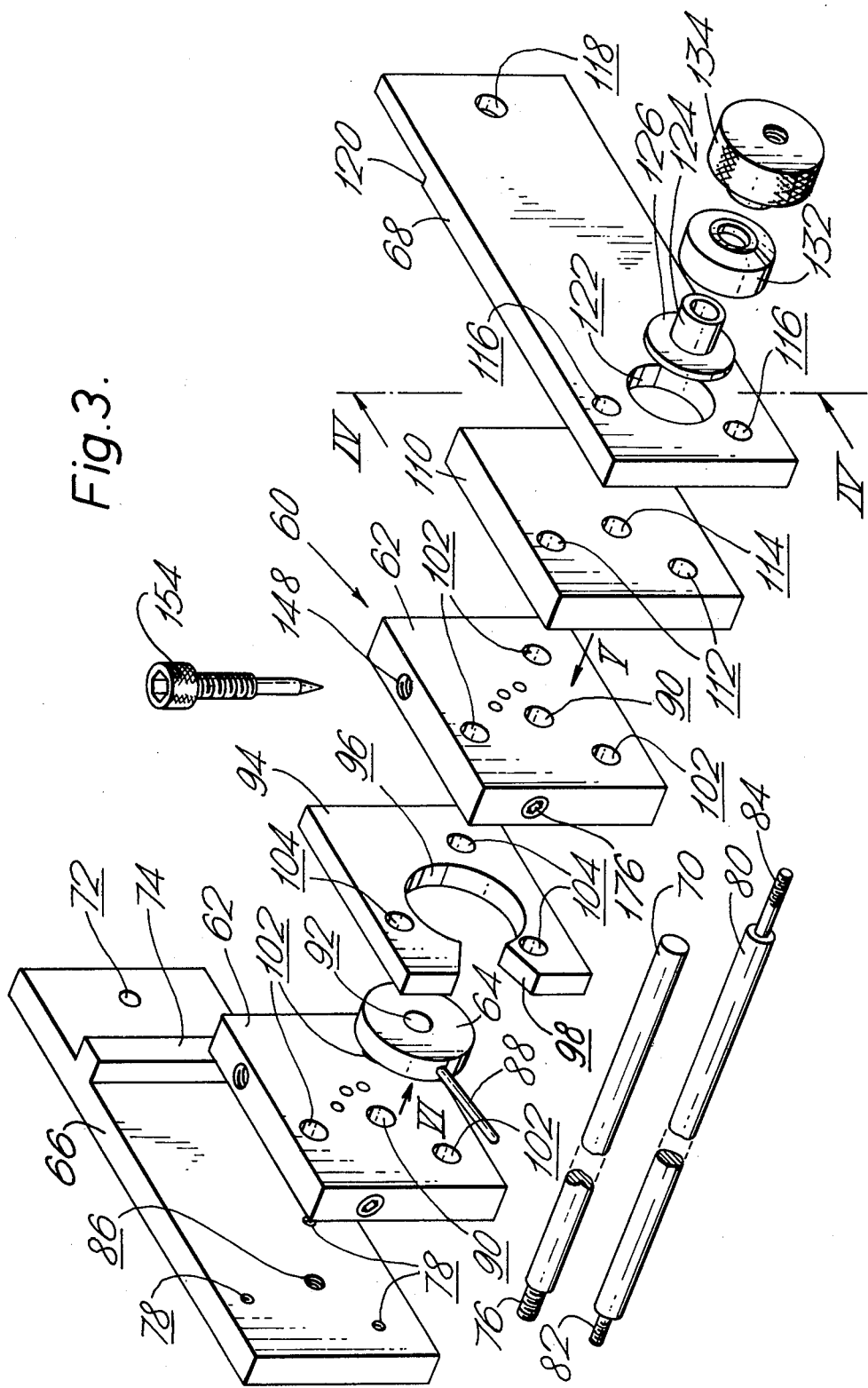
FIG. 3 is an exploded perspective view of the multiple valve assembly of FIG. 2.

Referring now to FIG. 3, the multiple valve assembly 60 comprises the thirty valve blocks 62 (only two of which are shown) and thirty diverter members 64 (only one of which is shown) supported between the left hand end plate 66 and the right hand end plate 68 by three guide rods 70 (only one of which is shown). When assembled, the left hand end plate 66 is attached by the bolt 46 (see FIG. 2) through a hole 72 onto the casing 44 (see FIG. 2), a ridge 74 on the end plate 66 abutting the casing 44 and preventing rotation of the assembly 60. Each of the guide rods 70 has a threaded portion 76 of reduced diameter at one end which engages in one of three internally threaded holes 78 through the left hand end plate 66 situated equidistant from each other and thus defining the corners of an equilateral triangle. An axle rod 80 has a threaded portion of reduced diameter at each end, 82 and 84 respectively, one threaded portion 82 engaging in an internally threaded axial hole 86 in the left hand end plate 66 at the centre of the triangle defined by the holes 78. The valve blocks 62, of rectangular shape, and the diverter members 64, of cylindrical shape, are of polytetrafluoroethylene (PTFE) and are located alternately along the length of the axle rod 80. A handle 88 extends radially from each diverter member 64. The axle rod 80 passes through a central hole 90 in each valve block 62 and through a central hole 92 in each diverter member 64.

A spacer 94, also of PTFE, of generally rectangular shape and slightly less thick than the axial thickness of the diverter members 64, surrounds each diverter member 64, and has a central hole 96 to accommodate the diverter member 64, with a keyhole shaped slot 98 at one side to allow the handle 88 (and hence the diverter member 64) to turn about the axle rod 80 through an angle of about 32°.

The three guide rods 70 extend parallel to the axle rod 80 through three equi-spaced holes 102 through each valve block 62, and through three equi-spaced holes 104 through each spacer member 94. Adjacent to the thirtieth diverter member 64 along from the left hand end plate 66, is a PTFE end block 110 of rectangular shape with three holes 112 (only two of which are shown) to locate the guide rods 70 and a hole 114 to locate the axle rod 80. The guide rods 70 extend through three equi-spaced holes 116 (only two of which are shown) in the right hand end plate 68 which is attached by the bolt 48 (see FIG. 2a) through a hole 118 to the casing 44 of the electrophoretic separator 10, a step 120 on the plate 68 abutting the casing 44 to prevent rotation of the assembly 60. As shown in FIG. 4, the axle rod 80 extends through a central hole 122 in the right hand end plate 68, in which is located a tubular disc support 124 with a flange 126. The flange 126 is resiliently urged into contact with the end block 110 by four annular disc springs 130 disposed between the flange 126 and an outer, annular disc spring support 132 retained by knurled nut 134 engaging with the threaded portion 84 of the axle rod 80. Rotation of the knurled nut 134 consequently adjusts the resilient force between the valve blocks 62 and the diverter members 64 along the entire length of the multiple valve assembly 60.

As shown in FIG. 5, each valve block 62 has an inlet port 140 (not shown in FIG. 3) to which the tube 42 (see FIG. 2) is connected, the inlet port 140 comprising a stainless steel stub pipe fitting 142 engaging in a threaded hole 143 in one side of the block 62 and forming a liquid-tight seal therein. From the hole 143 a narrow cylindrical hole 144 communicates with a cylindrical valve hole 146 extending from a threaded hole 148 perpendicular to the hole 144. One end of the valve hole 146 communicates with an inlet valve port 150 extending from a plane face 152 of the valve block 62. A valve stem 154 has a threaded portion 156 which engages in the threaded hole 148, rotation of the stem 154 controlling the rate of flow of liquid through the inlet port 140 in operation of the valve assembly 60. The valve stem 154 is of such a diameter as to engage in the valve hole 146 and so form a liquid-tight seal.

Each valve block 62 also has a first outlet port 160 and a second outlet port 162, (not shown in FIG. 3) to which the outlet tubes 54 and 56 (see FIG. 2) respectively connect, and comprising stainless steel stub pipe fittings 142 engaging in respective threaded holes 164 and 165 in the block 62 and forming liquid-tight seals therein. A narrow cylindrical hole 166 extends from the threaded hole 164 to communicate with a first valve port 168 extending from the plane face 152 of the block 62, and a narrow cylindrical hole 170 extends from the threaded hole 165 to communicate with a cylindrical hole 172 perpendicular to the hole 170 and communicating at one end with a second valve port 174 extending from the plane face 152 of the block 62. The other end of the hole 172 is sealed by a screw plug 176 locating in a threaded hole 178. The inlet valve port 150, the first valve port 168, and the second valve port 174, lie on an arc of a circle concentric with the central hole 90, the inlet valve port 150 being midway between the first valve port 168 and the second valve port 174, at an angle of about 30 degrees along the arc from each.

As shown in FIGS. 6 and 6a each diverter member 64 has a shallow, concentric arcuate groove 180 on one face 182. When the valve assembly 60 is assembled, the face 182 abuts the plane face 152 of the adjacent valve block 62. The arcuate groove 180 extends through an angle of about 32 degrees, and so provides communication between the inlet valve port 150 and either the first valve port 168 or the second valve port 174, depending on the orientation of the handle 88.

In operation of the valve assembly 60, when the thirty inlet ports 140 are connected by the tubes 42 to the thirty discharge ducts 40 carrying the outlet streams from the electrophoretic separator 10, the valve assembly 60 enables each of the thirty outlet streams to be diverted independently to either the first outlet port 160 or the second outlet port 162 of the respective valve block 62 and hence to the outlet tube 54 or 56, by moving the appropriate handle 88, and enables the flow rate of each outlet stream to be controlled independently by turning the respective valve stem 154. The setting of this flow rate is independent of which outlet port, 160 or 162, is in use.

In some applications it may be advantageous to divert each outlet stream simultaneously and to the same respective first outlet port 160 or second outlet port 162, and one means by which this may be accomplished is shown in FIG. 7, to which reference is now made.

In FIG. 7, the multiple valve assembly 60 of FIG. 2 (shown chain dotted) has been modified by the addition of a switching device 190. The switching device 190 comprises an anodised aluminium alloy switching bar 192 of length slightly greater than the multiple valve assembly 60 with a rectangular groove 194 along one side to engage simultaneously with all thirty handles 88 (only one is shown) of the multiple valve assembly 60. The switching bar 192 is supported at each end by a respective stainless steel bar 196, 197. Each bar 196, 197 has one end thereof of reduced width to engage a shallow rectangular slot 198 across the end of the switching bar 192, and is pivotally supported at the other end thereof by a pivot pin 200 (only the right hand pivot pin 200 is shown) projecting from a spacer pillar 202 joined to the respective end plate 66 or 68 of the multiple valve assembly 60 by a threaded stub 203 (only the right hand stub 203 is shown and in broken line). To the left hand end of the switching bar 192, the bar 197 is attached by a countersunk screw 204, while from the right hand end of the switching bar 192 a threaded rod 206 extends through a clearance hole (not shown) in the bar 196 to engage with an internally threaded knurled knob 208.

The switching device 190 is thus pivotable about the pivot pins 200, and thereby simultaneously operates the thirty handles 88 of the multiple valve assembly 60. The pivotal motion of the switching device 190 is limited, because the handles 88 can only turn through the angle 32° determined by the width of the slots 98 in the spacer members 94.

If it is desired to operate the handles 88 independently, the switching device may readily be removed from the multiple valve assembly 60 by slackening the knurled knob 208. The bars 196 and 197 can then be removed from their respective pivot pins 200.

Although the electrophoretic separator 10 has been described as having thirty discharged ducts 40, and the multiple valve assembly 60 as having thirty valve blocks 62 and thirty diverter members 64, it will be appreciated that the number of discharge ducts 40, and consequently of valve blocks 62 and diverter members 64 may be different from thirty. It will also be appreciated that the orientations of the inlet port 140 and the first and second outlet ports 160 and 162 on each valve block 62 may be different from those shown, to suit particular applications, as also may be the angle through which the handle 88 moves, and an example of an alternative valve block is shown in FIG. 8.

In FIG. 8 is shown a sectional view through a rectangular PTFE valve block 210 of an alternative multiple valve assembly 212, similar to the multiple valve assembly 60 of FIG. 2, identical components being referred to by the same reference numerals. The multiple valve assembly 212 comprises thirty valve blocks 210, each supported by four guide rods 70 and an axle rod 80, and each having an inlet port 140 on its upper surface, a first outlet port 160 on its lower surface, and a second outlet port 162 on its rear surface. The inlet port 140 comprises a stub pipe fitting 142 engaging in a threaded hole 214 and forming a liquid-tight seal therein. A cylindrical hole 216 extends perpendicular to the hole 214, the hole 216 at one end being sealed by a screw plug 176 engaging in a threaded portion 218 of the hole 216, and the other end communicating with a valve hole 220. One end of the valve hole 220 communicates with an inlet valve port (not shown) extending from a plane face of the valve block 210. A valve stem 154 has a threaded portion 156 which engages in the valve hole 220, rotation of the valve stem 154 controlling the rate of flow of liquid through the inlet port 140.

The first outlet port 160 and the second outlet port 162 each comprises a stub pipe fitting 142 engaging in a respective threaded hole 222, 224 and forming a liquid-tight seal therein, each theaded hole 222, 224 communicating with a respective first outlet valve port or second outlet valve port (not shown) extending from the said plane face of the valve block 210. The inlet valve port, and the first and the second outlet valve ports lie on an arc of a circle concentric with the axle rod 80. Adjacent to each said plane face is a diverter member 64 (not shown) from which extends a handle 88, and which provides communication between the inlet valve port and either the first or the second outlet valve port, depending on the orientation of the handle 88, as explained in relation to FIGS. 5 and 6, the multiple valve assembly 212 operating in the same manner as the multiple valve assembly 60 of FIG. 2.

Mounted below the multiple valve assembly 212 is a stainless steel trough 230 to catch any drips of liquid which may emerge from between adjacent valve blocks 210 and diverter members 64 during operation of the multiple valve assembly 212. From the base of the trough 230 extends a drain tube 232. The trough 230 is provided with a hinged flap portion 234 extending the width of the multiple valve assembly 212, to provide access to any liquid streams emerging from the first outlet ports 160. The trough 230 has an upper edge 236 that forms a splash-tight seal with the rear of the multiple valve assembly 212, and the upper edge of the flap portion 234 when closed forms a seal with the front of the multiple valve assembly 212, to protect an operator from hazards arising from drips of any toxic material from the multiple valve assembly 212. If it is desired to take a sample of an outlet stream, a sampling device (not shown) may be inserted into the trough 230 after opening the flap 234, and the appropriate handle 88 turned to divert the outlet stream to the corresponding first outlet port 160. After a sample has been taken, the outlet stream may be diverted back to an outlet tube 56 (not shown) connected to the second outlet port 162.

For convenience the groove 180 in the diverter member 64, which provides communication between the inlet valve port 150 and either the first valve port 168 or the second valve port 174 of the adjacent valve block 62 or 210, is defined in a plane face 182 of the diverter member 64. Alternatively the face of a diverter member, in which a groove is defined, may be curved, and adjacent to a correspondingly curved face of a valve block in which inlet and outlet valve ports are defined.

I claim:

1. A continuous flow electrophoretic separator comprising, a rotor, a stator, an annular chamber defined between the rotor and the stator, and a plurality of discharge ducts communicating with the chamber, wherein there is provided a multiple valve assembly comprising a plurality of valve units, each valve unit beng connectable to one of the discharge ducts and comprising means for controlling and variably adjusting independently of the other valve units the rate of flow of a liquid therethrough, and means for diverting the liquid flowing through said valve unit to one of a plurality of outlet ports.

2. A separator as claimed in claim 1, wherein the diverting means comprises a valve body with an inlet port connectable to one of the discharge ducts, a plurality of outlet ports, an inlet valve port, a plurality of outlet valve ports, the valve body defining a duct communicating between the inlet port and the inlet valve port, and defining ducts each communicating between one of the outlet ports and a corresponding one of the outlet valve ports, and a diverter member defining a diversion duct and turnable about an axis between positions in which the diversion duct provides communication between the inlet valve port and any one of the outlet valve ports.

3. A separator as claimed in claim 2 wherein the inlet valve port, and the outlet valve ports extend from a plane face of the valve body.

4. A separator as claimed in claim 3 wherein the diverter member is of cylindrical form, having a plane face adjacent to the plane face of the valve body, and is located within a circular hole through a flat spacer member.

5. A separator as claimed in claim 4 wherein an operating handle projects from the cylindrical surface of the diverter member through a gap in the spacer member, the width of the gap being arranged to limit the rotational movement of the diverter member.

6. A separator as claimed in claim 2 wherein the diversion duct is defined by a groove on a face of the diverter member adjacent to the valve block.

7. A separator as claimed in claim 2 wherein each valve body has two said outlet ports, and the inlet valve port, the first outlet valve port and the second outlet valve port lie on an arc of a circle centred on the axis, the inlet valve port being between the first outlet valve port and the second outlet valve port.

8. A separator as claimed in claim 7, wherein the inlet valve port lies midway between the first outlet valve port and the second outlet valve port.

9. A separator as claimed in claim 2 including resilient means for biasing the valve bodies and diverter members together.

10. A separator as claimed in claim 9 wherein the resilient means includes means for adjusting the resilient bias thereof.

11. A separator as claimed in claim 2 wherein the control means comprises an adjustable obturator in the duct between the inlet port and the inlet valve port.

12. A separator as claimed in claim 1 wherein each diverting means is operable independently of the other diverting means.

13. A separator as claimed in claim 12 also comprising a switching means, demountably connected to the separator, for operating all the diverting means simultaneously to divert the respective liquid flow to the same respective outlet port.

14. A separator as claimed in claim 1 including a trough arranged to catch drips of liquid emerging in operation from the multiple valve assembly and adapted to allow access to one outlet port of each valve unit.

15. In a continuous flow electrophoretic separator comprising a rotor, a stator, an annular chamber defined between the rotor and the stator, and a plurality of discharge ducts communicating with the chamber, the improvement comprising a multiple valve assembly comprising:

(a) a plurality of valve bodies, each valve body having an inlet port connectable to one of the discharge ducts, and two outlet ports; and having an inlet valve port a first outlet valve port and a second outlet valve port extending from a plane face of the valve body; each valve body defining a duct communicating between the inlet port and the inlet valve port, and ducts communicating respectively between one of the outlet ports and the first or the second outlet valve ports;

(b) a plurality of adjustable obturators, each located in the duct between the inlet port and the inlet valve port of a respective valve body, for controlling and variably adjusting the rate of flow of liquid through the respective valve body;

(c) a plurality of cylindrical diverter members, each with a plane face adjacent to the plane face of one of the valve bodies and turnable about an axis between two positions, a groove on the plane face of the diverter member providing communication between the inlet valve port and either the first or the second outlet valve port of the said one of the valve bodies;

(d) a plurality of flat spacer members each defining a circular hole to locate one of the diverter members; and (e) adjustable resilient clamping means for urging the valve bodies and the diverter members together in alternate relationship.

16. A separator as claimed in claim 15, including a switching bar, side members pivotally connecting the bar to the separator, and a respective rod member connected at one end to each diverter member and located at the other end thereof in a groove defined by the bar, so that pivotal movement of the bar causes all the diverter members to turn.

* * * * *